United States Patent
Kataria et al.

(10) Patent No.: US 12,002,580 B2
(45) Date of Patent: Jun. 4, 2024

(54) SYSTEM AND METHOD FOR CUSTOMIZED PATIENT RESOURCES AND BEHAVIOR PHENOTYPING

(71) Applicant: Mytonomy Inc., Bethesda, MD (US)

(72) Inventors: Anjali Kataria, Chevy Chase, MD (US); Vinay Bhargava, Chevy Chase, MD (US)

(73) Assignee: MYTONOMY INC., Chevy Chase, MD (US)

( * ) Notice: Subject to any disclaimer, the term of this patent is extended or adjusted under 35 U.S.C. 154(b) by 262 days.

(21) Appl. No.: 16/037,994

(22) Filed: Jul. 17, 2018

(65) Prior Publication Data

US 2019/0027248 A1    Jan. 24, 2019

Related U.S. Application Data

(60) Provisional application No. 62/533,939, filed on Jul. 18, 2017.

(51) Int. Cl.
*G16H 50/20* (2018.01)
*G06N 3/08* (2023.01)
(Continued)

(52) U.S. Cl.
CPC ............ *G16H 50/20* (2018.01); *G06N 3/08* (2013.01); *G06N 20/00* (2019.01); *G10L 25/63* (2013.01);
(Continued)

(58) Field of Classification Search
CPC ........ G16H 50/20; G16H 20/70; G16H 50/70; G16H 10/20; G16H 10/60; G16H 40/20;
(Continued)

(56) References Cited

U.S. PATENT DOCUMENTS 8,402,161 B2   3/2013   DelloStritto et al.
8,996,428 B2   3/2015   Baras et al.
(Continued)

FOREIGN PATENT DOCUMENTS

WO   2017/025573 A1   2/2017

OTHER PUBLICATIONS

Vivify Health Awarded Patent for Extending EMRs with Digital Health; CISION PR Newswire; News provided by Vivify Health;<http://www.prnewswire.com/news-releases/vivify-health-awarded-patent-for-extending-emrs-with-digital-health-300442448.html>; Apr. 20, 2017; 4 pages.

(Continued)

*Primary Examiner* — Peter H Choi
*Assistant Examiner* — Shyam M Goswami
(74) *Attorney, Agent, or Firm* — Michele V. Frank; Venable LLP

(57) ABSTRACT

Systems and methods to improve use of patient prescribed video materials by (1) providing patients with the right amount of resources/time that they individually need, where the resources/time are determined based on quantifiable metrics recorded by clinically validated instruments as well as other data; (2) classifying and segmenting patients into behavioral phenotypes based on real-time responses and predicting healthcare utilization, adherence, and trajectory of the patient; and (3) based on the predictions, generating a customized microlearning video library, tailored to the patient's needs and abilities. These improvements and efficiencies can be provided through a cloud-based enterprise computing architecture based on communications made directly to wireless devices controlled by the patient.

19 Claims, 7 Drawing Sheets

(51) Int. Cl.
*G06N 20/00* (2019.01)
*G10L 25/63* (2013.01)
*G16H 10/20* (2018.01)
*G16H 20/70* (2018.01)
*G16H 50/70* (2018.01)
*H04N 7/18* (2006.01)

(52) U.S. Cl.
CPC .............. *G16H 10/20* (2018.01); *G16H 20/70* (2018.01); *G16H 50/70* (2018.01); *H04N 7/183* (2013.01)

(58) Field of Classification Search
CPC ........ G16H 40/63; G16H 80/00; G16H 40/67; G06N 3/08; G06N 20/00; G10L 25/63; H04N 7/183; G06F 19/30; G06F 19/32; G06F 19/34; G06F 19/36; G06F 3/0484; G06Q 50/22; G06Q 50/24; A61B 5/00; A61B 5/145; A61B 5/168; A61B 5/1118; A61B 5/4815; A61B 5/165; H04L 29/08; H04L 12/24
See application file for complete search history.

(56) References Cited

U.S. PATENT DOCUMENTS

| | | |
|---|---|---|
| 9,357,238 B2 | 5/2016 | Rock |
| 9,495,554 B2 | 11/2016 | Kapoor |
| 9,619,849 B2 | 4/2017 | Rock |
| 2003/0212579 A1* | 11/2003 | Brown .................. G16H 10/60 705/2 |
| 2004/0138924 A1 | 7/2004 | Pristine |
| 2004/0243433 A1 | 12/2004 | Akin et al. |
| 2008/0051640 A1 | 2/2008 | Iliff |
| 2008/0260212 A1 | 10/2008 | Moskal et al. |
| 2009/0018407 A1 | 1/2009 | Jung et al. |
| 2009/0248444 A1 | 10/2009 | Harnick |
| 2011/0229864 A1 | 9/2011 | Short et al. |
| 2013/0086477 A1 | 4/2013 | Newrai |
| 2014/0114680 A1 | 4/2014 | Mills et al. |
| 2014/0297301 A1 | 10/2014 | Rock |
| 2014/0298260 A1 | 10/2014 | Abowd et al. |
| 2014/0335490 A1 | 11/2014 | Baarman et al. |
| 2014/0337223 A1 | 11/2014 | Kapoor |
| 2014/0349262 A1 | 11/2014 | Mason et al. |
| 2014/0372138 A1 | 12/2014 | Chari et al. |
| 2015/0086947 A1* | 3/2015 | Schweid .................. G09B 5/06 434/219 |
| 2015/0099946 A1 | 4/2015 | Sahin |
| 2015/0223731 A1* | 8/2015 | Sahin .................. A61B 5/1123 600/301 |
| 2015/0332017 A1* | 11/2015 | Swanson ................ G16H 40/67 705/3 |
| 2016/0140320 A1* | 5/2016 | Moturu .................. G16H 50/30 434/236 |
| 2016/0246928 A1 | 8/2016 | Rock |
| 2016/0371992 A1 | 12/2016 | Kozloski et al. |
| 2017/0312289 A1* | 11/2017 | Dugan Stocks ........ A61P 25/14 |
| 2018/0264209 A1* | 9/2018 | Hazani .................. A61M 15/00 |
| 2019/0311790 A1* | 10/2019 | Dadkhahnikoo ...... G16H 80/00 |

OTHER PUBLICATIONS

International Search Report and Written Opinion in corresponding International Application No. PCT/US18/42540 dated Sep. 28, 2018 (9 pages).
Extended European Search Reported dated Mar. 15, 2021, directed to EP Application No. 18834739.7, 11 pages.
Communication pursuant to Article 94(3) dated Apr. 17, 2023, directed to EP Application No. 18834739.7; 12 pages.

* cited by examiner

SYSTEM AND METHOD FOR CUSTOMIZED PATIENT RESOURCES AND BEHAVIOR PHENOTYPING

PRIORITY

The present application claims priority to U.S. Provisional Application No. 62/533,939, filed Jul. 18, 2017, the contents of which are incorporated herein in their entirety.

BACKGROUND

1. Technical Field

The present disclosure relates to allocation of resources for healthcare patients, and more specifically to predicting patient responsiveness and success in self-care of patient's condition based on real-time analysis.

2. Introduction

When patients visit healthcare facilities (such as clinics, hospitals, private practices, etc.), a common practice of scheduling follow up appointments or treatments is to classify the patients as new patients (first time to the clinic or practice) or follow up appointments (those that have been seen before), and making the follow up schedules based on the classification and prior experience with that patient. In some cases, human medical staff may attempt to classify patients based on the questions the patients ask, the staff's own superficial observations, or by a generic categorization (i.e. all patients that had surgery get a 45 min follow up appointment, or all new insulin starts get a 50 minute follow up appointment with a nurse educator). However, this inefficient and ineffective method of trying to accurately match patient's subsequent healthcare resourcing needs with the available healthcare resources has not resulted in improved care, reduced cost or faster cycle times. Furthermore, the treatment plan that is given to a patient with a condition is fairly standard to the patient's condition and does not factor in personalized, tailored information that would allow for a more tailored treatment protocol. For example, diabetes patients starting insulin are given a new insulin user handout or signed up for a multi-week class, with no special information or treatment provided based on a patient's individual ability to manage their insulin dosing correctly. As an extreme, imagine if in other types of business, every appointment with every client was for the same amount of time, regardless of the client's needs and ability, or the time required to reach an informed conclusion. For example, imagine if every shopper who went to a store for clothes was handed tennis shoes, a white button down shirt, and there was no information gathered from the consumer to determine which type of shoe, which style color, what shirt size, etc., would be most appropriate to meet the needs of each specific customer based on their behavior, lifestyles, attitudes, bias etc. This would be very inefficient, and is how the typical healthcare system treats patients when scheduling patient appointments or providing patient instructions.

Similar, "one size fits all" solutions for healthcare are highly inefficient and do not take into account the patient's likelihood of success with their self-care (those things for which the patient is responsible, such as reading clinician-provided information and applying that information to their own self-care or taking prescription medicines). Moreover, the type of self-care prescribed may vary based on numerous behavioral and lifestyle factors which only the patient knows, and issuing one size fits all directions in the absence of this important healthcare engagement and behavioral information as reported by patients themselves perpetuates the inefficiencies present in the system.

SUMMARY

The concepts and disclosure provided herein reduce the inefficiencies of the previous system by (1) providing patients with the right amount of resources/time that they individually need prior to, in between, and after visits as well as during the visit, where the resources/time are determined based on quantifiable metrics recorded by clinically validated instruments as well as other data; (2) classifying, segmenting, and phenotyping patients based on real-time responses to behavioral and engagement surveys, and predicting healthcare utilization, adherence, and trajectory of the patient; and (3) based on the predictions, generating a customized, curated, microlearning video library, tailored to the patient's needs and abilities, with each instruction video customized to the patient based on their patient behavior score, risk and self-reported information. These improvements and efficiencies can be provided through a cloud-based enterprise computing architecture based on communications made directly to wireless devices controlled by the patient. The goal of tailoring healthcare instructions and resources, and phenotyping the patient into specific categories based on online engagement and behavioral science, is to enable the patient to more successfully manage themselves outside of the health system, across their entire care continuum, and provide better information to the clinical team.

To provide patients with the right amount of resources/time that they individually need, resource allocation recommendations can be made to staff at the healthcare facility based on instant, real-time information as the patients arrive at the healthcare facility (or in real-time before the patients arrive if completing an online questionnaire remotely), and these healthcare resources can be further allocated based on past behavior of the patient. The arriving patients are classified along a multi-dimensional spectrum spanning activation levels, quality of life, anxiety and/or depression, attitudes, beliefs and perceptions, where the individual activation levels can indicate how likely the patients are to follow general instructions, specific instructions, and/or respond to the therapy/procedures/medicines prescribed. The spectrum is multi-dimensional in that each factor can act as a dimension in the respective activation level or behavior class being classified. For example, patients which are the ranked highest on a particular activation level can be recommended for shorter appointments, with less intrusive or less costly resources. Those patients which are lower on that same activation level can be recommended for longer appointments and more intensive resources. Those patients with negative attitudes towards their diseases can be prescribed a peer-buddy or watch peer-videos to give them a different "model." Those that are anxious and lower activation can be prescribed clinician videos that contain content known to address this behavioral type, to better engage them versus using the same content a higher ranked activation patient with no anxiety would get. Using the activation levels, behavior (past and/or present), anxiety or distress measures, medical condition/diagnosis, and/or other information about the patient, a behavior profile can be generated for the patient. Each behavior profile is unique to each patient, but will fall within a range and the classification is not by condition as our healthcare system is currently.

Based on the behavior profile obtained, patients can be classified/segmented into distinct categories, and can receive healthcare services based on that segmentation and their phenotype. This categorization of the patients, or phenotyping, can be used to tailor patient visits as well as the services provided after the visit. For example, if a patient is categorized as likely to understand a diagnosis a relatively short doctor visit can be scheduled, whereas if the patient is categorized as unlikely to understand the diagnosis the scheduled visit can be longer. Likewise, if additional care is needed with a specific aspect of the patient's care (i.e., a concern with needles associated with insulin), adjustments can be made to reflect that extra care, and that patient's microlearning video instruction library can reflect the appropriate content for that particular patient's needs. In this manner, the patients can be classified into distinct risk pools which categorize the healthcare utilization, adherence, and health trajectory of the patient. All of this is done in real-time by accessing multiple databases and resources, and provides efficiencies and benefits to the healthcare process which human beings alone are incapable of achieving (namely speed, accuracy, lack of prejudice, database access, and weighted calculations, all done in real-time in response to patient self-reported answers, and which may also include voice and facial analysis).

Furthermore, these categorizations and segmentations can allow the system to generate education tools which are specifically tooled to assist that individual patient. More specifically, based on the behavior phenotype generated for the patient, and the diagnosis of the patient from the EMR, and the patient's pattern of completing assignments (i.e., taking medicine, watching videos, read educational materials, etc.), patient activation level, anxiety level, and/or other information (including demographics, content viewership, online engagement at other sites, other patient preferences and behavior indicators such as depression, anxiety, distress as well as other data which may be used in generating the behavior phenotype), the system can generate a library of videos for the patient to watch. In a preferred configuration, the library of videos would incorporate microlearning, where each video is between 15 seconds and 3 minutes long, where the videos selected (and the order of the videos) are selected based on the specific data associated with that patient. In some configurations, the videos are pre-recorded to specific lengths, then selected for inclusion into the libraries of specific patients. In other configurations, the system can rapidly edit a longer video to the desired length and content required for a patient, then place the edited version of the video into the patient's library. This is all done through self service capabilities, versus third party video production shops making the edits.

An exemplary method performed according to the concepts disclosed herein can include: receiving, from a mobile device, answers to a behavioral questionnaire, wherein the answers are received in real-time as a patient completes the behavioral questionnaire on the mobile device; generating, via a processor and based on the answers, at least one clinically validated behavioral score; recording a video of the patient as the answers are completed; identifying, via the processor and based on the video of the patient, at least one expression of the patient made during completion of the behavioral questionnaire; calculating a score of the patient based upon the at least one clinically validated behavioral score and the at least one expression; receiving a medical condition of the patient; and generating a library of videos customized to the patient based upon at least (1) the score and (2) the medical condition.

An exemplary system configured according to this disclosure can include: a video capture device; a processor; and a computer-readable storage medium having instructions stored which, when executed by the processor, cause the processor to perform operations including: receiving, from a mobile device, answers to a behavioral questionnaire, wherein the answers are received in real-time as a patient completes the behavioral questionnaire on the mobile device; generating, based on the answers, at least one clinically validated behavioral score; recording, via the video capture device, a video of the patient as the answers are completed; identifying, based on the video of the patient, at least one expression of the patient made during completion of the behavioral questionnaire; calculating a score of the patient based upon the at least one clinically validated behavioral score and the at least one expression; receiving a medical condition of the patient; and generating a library of videos customized to the patient based upon at least (1) the score and (2) the medical condition.

An exemplary non-transitory computer-readable storage medium configured according to this disclosure can have instructions stored which, when executed by a computing device, can cause the computing device to perform operations including: receiving, from a mobile device, answers to a behavioral questionnaire, wherein the answers are received in real-time as a patient completes the behavioral questionnaire on the mobile device; generating, based on the answers, at least one clinically validated behavioral score; recording a video of the patient as the answers are completed; identifying, based on the video of the patient, at least one expression of the patient made during completion of the behavioral questionnaire; calculating a score of the patient based upon the at least one clinically validated behavioral score and the at least one expression; receiving a medical condition of the patient; and generating a library of videos customized to the patient based upon at least (1) the score and (2) the medical condition.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

DETAILED DESCRIPTION

Figure 1:
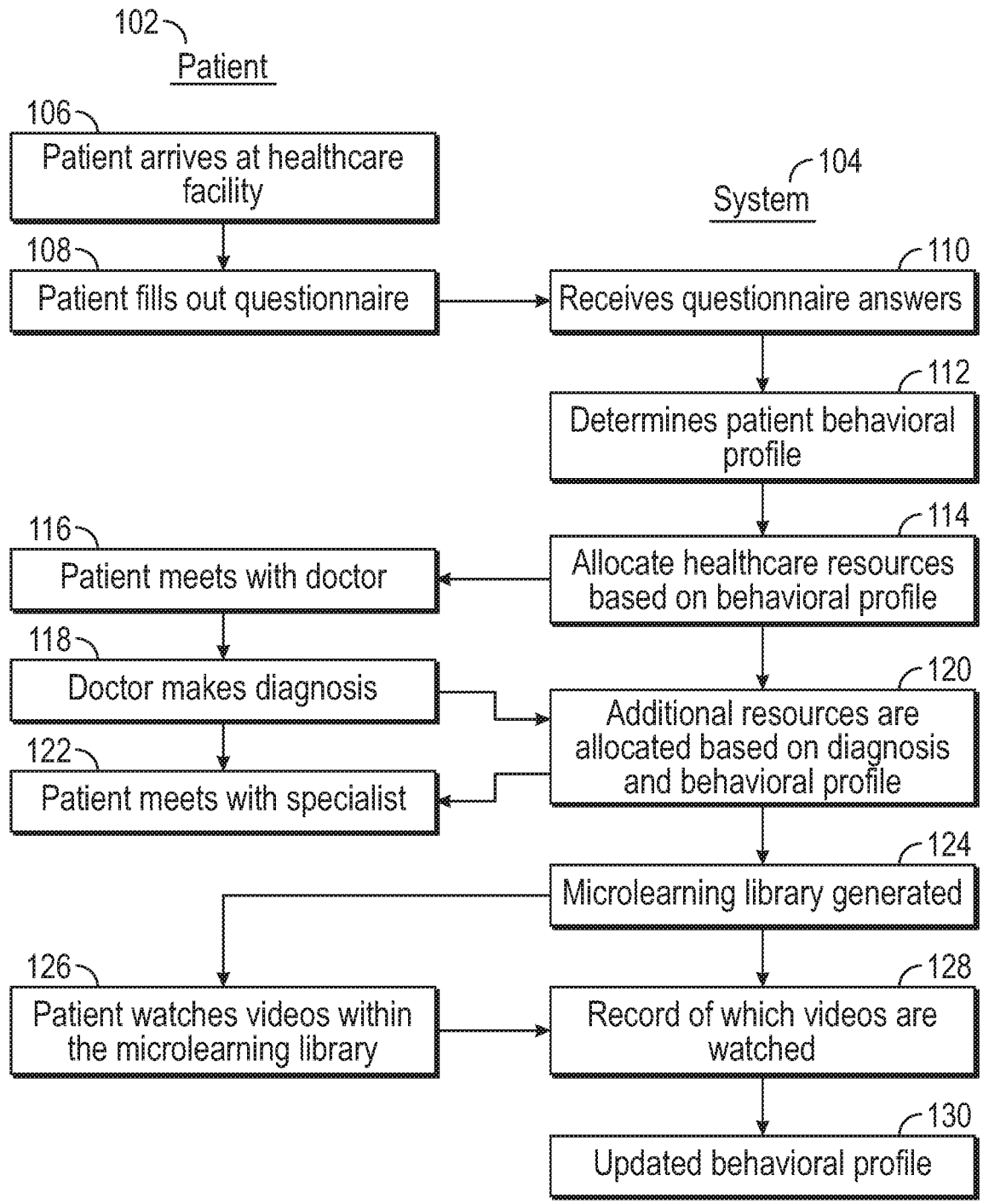
FIG. 1 illustrates an exemplary flow chart relating patient actions to system performance.

The concepts and disclosure provided herein reduce the inefficiencies of the previous system by (1) providing patients with the right amount of resources/time that they individually need, where the resources/time are determined based on quantifiable metrics recorded by clinically validated instruments as well as other data; (2) classifying and segmenting (i.e., phenotyping) patients based on real-time responses and predicting healthcare utilization, adherence, and trajectory of the patient; and (3) based on the predictions, generating a customized microlearning video library, tailored to the patient's needs and abilities. These improvements and efficiencies can be provided through a cloud-based enterprise computing architecture based on communications made directly to wireless devices controlled by the patient.

The disclosed system can provide patients with the right amount of resources/time that they individually need, with resources allocated based on instant, real-time information. These allocations can occur before a patient ever arrives at a healthcare facility. For example, if the patient completes an online survey or questionnaire, the results can be used to modify what resources are being provided to the patient. Likewise, as the patients arrive at the healthcare facility, how the patient completes questionnaires, or patient behavior while on-site, can be used to modify patient allocated resources. After the patient leaves, patient reported outcomes (such as the patient reporting the taking of medications) and automatically reported patient behavior (such as reporting of the patient watching a video) can be further used to allocate, or re-allocate, resources.

Moreover, the patients can be clustered, or phenotyped, based upon their behavioral profile. The behavioral profile can be generated based on a combination of clinical behavior measures (how the patient corresponds to clinical determinations) with quantitative behavior measures (specific data points, such as a viewership record, pattern of following instructions, gestures, voice patterns (inflections, pauses, etc.), time filling out a questionnaire, etc.). As part of the process for developing a behavioral profile for each patient, patients can be classified along a multi-dimensional activation level spectrum, where the activation level indicates how likely the patients are to follow instructions and respond to the therapy/procedures/medicines prescribed. Patients which are the ranked highest on the activation level spectrum can be recommended for shorter appointments, with less intrusive or less costly resources. Those patients which are lower on the activation level spectrum can be recommended for longer appointments and more intensive resources. Activation levels can be part of a weighted function to develop the behavioral profile. This weighted function can use a series of scores, where the series of scores is based on real-time metrics, activation levels obtained from the patient as they fill out a questionnaire on a mobile computing device (such as a smartphone, laptop, tablet, etc.), as well as non-real-time data such as demographics, etc. In addition, voice and facial recognition can be an input into the equation to counter balance the self-reporting bias that sometimes exists.

The scores can be calculated at the time of patient intake, and can include, for example:

(1) A series of clinically validated instruments including: PAM (Patient Activation Measure, a commercial product proven to asses a patient's understanding in managing their health and the patient's skill level in managing their health), Stanford Self-Efficacy, Beck's depression inventory (a test to determine depression within a patient), PH2 anxiety a clinically validated anxiety measure, P2 Depression, a clinically validated depression measure, Kansas Quality of Life, WHO-5 (a clinically validated measure of quality of life), a clinically determined attitude towards insulin survey, a clinically validated adherence survey, and other clinically validated instruments as well as clinically validated questions related to Satisfaction, Ease of Use, Usefulness of Content, etc.

(2) Patient Reported Outcomes. This can include self-reported answers to symptoms, experience, expectations, and attitudes, and can be reported via a survey or questionnaire upon arriving at the healthcare facility or pre-arrival delivered via a mobile responsive enterprise system. Table 1 contains exemplary questions which can be presented to a patient, and though these reflect a diabetes patient, similar questions could be constructed and used for other conditions. The key point is to take a validated survey plus homegrown questions, plus facial and/or voice analysis are combined together along with the passive data from their online engagement of video viewership to create a behavioral and engagement phenotype of the patient to then allocate resources. Below are examples of the types of questions being asked across multiple disciplines:

TABLE 1

| | |
|---|---|
| Please indicate your profession | General Practitioner, Specialist physician, Nurse, Other, please specify |
| Did you receive the influenza vaccination last influenza season? (check the box) [move this Q and the next one to the end, as they are STAFF q's not patient. | Yes (1) No (0) |
| How important do you believe it is to discuss influenza vaccination with your patients with diabetes? | 1 to 5 scale (1 = not at all important-5 = highly important) |
| How frequently do you recommend influenza vaccination to your patients with diabetes? | 1 to 5 scale (1 = not at all important-5 = highly important) |
| When all is said and done, I am the person who is responsible for taking care of my health | Disagree Strongly (1) Disagree (2) Agree (3) Agree Strongly (4) N/A |
| Taking an active role in my own health care is the most important thing that affects my health | Disagree Strongly (1) Disagree (2) Agree (3) Agree Strongly (4) N/A |
| I am confident I can help prevent or reduce problems associated with my health | Disagree Strongly (1) Disagree (2) Agree (3) Agree Strongly (4) N/A |
| I know what each of my prescribed medications do | Disagree Strongly (1) Disagree (2) Agree (3) Agree Strongly (4) N/A |
| I am confident that I can tell whether I need to go to the doctor or whether I can take care of a health problem myself | Disagree Strongly (1) Disagree (2) Agree (3) Agree Strongly (4) N/A |
| I am confident that I can tell a doctor concerns I have even when he or she does not ask | Disagree Strongly (1) Disagree (2) Agree (3) Agree Strongly (4) N/A |

TABLE 1-continued

| Please indicate your profession | General Practitioner, Specialist physician, Nurse, Other, please specify |
|---|---|
| I am confident that I can follow through on medical treatments I may need to do at home | Disagree Strongly (1) Disagree (2) Agree (3) Agree Strongly (4) N/A |
| I understand my health problems and what causes them | Disagree Strongly (1) Disagree (2) Agree (3) Agree Strongly (4) N/A |
| I know what treatments are available for my health problems | Disagree Strongly (1) Disagree (2) Agree (3) Agree Strongly (4) N/A |
| I have been able to maintain (keep up with) lifestyle changes, like eating right and exercising | Disagree Strongly (1) Disagree (2) Agree (3) Agree Strongly (4) N/A |
| I know how to prevent problems with my health | Disagree Strongly (1) Disagree (2) Agree (3) Agree Strongly (4) N/A |
| I am confident I can figure out solutions when new problems arise with my health | Disagree Strongly (1) Disagree (2) Agree (3) Agree Strongly (4) N/A |
| I am confident that I can maintain lifestyle changes, like eating right and exercising, even during times of stress | Disagree Strongly (1) Disagree (2) Agree (3) Agree Strongly (4) N/A |
| I am worried about taking insulin | Strongly Disagree (1) Disagree (2) Somewhat Disagree (3) Somewhat Agree (4) Agree (5) Strongly Agree (6) |
| I am not sure I can manage my diabetes with insulin | Strongly Disagree (1) Disagree (2) Somewhat Disagree (3) Somewhat Agree (4) Agree (5) Strongly Agree (6) |
| I don't know if insulin will make my condition worse | Strongly Disagree (1) Disagree (2) Somewhat Disagree (3) Somewhat Agree (4) Agree (5) Strongly Agree (6) |
| How confident are you about answering patients' questions about influenza vaccination? | 1 to 5 scale (1 = not at all important-5 = highly important) |
| I am satisfied with this video education | Strongly Disagree (1) Disagree (2) Somewhat Disagree (3) Somewhat agree (4) Agree (5) Strongly Agree (6) |
| In general, I am satisfied with the amount of information and education given to me | Strongly Disagree (1) Disagree (2) Somewhat Disagree (3) Somewhat agree (4) Agree (5) Strongly Agree (6) |
| This system was easy to use. | Strongly Disagree (1) Disagree (2) Somewhat Disagree (3) Somewhat agree (4) Agree (5) Strongly Agree (6) |
| It was easy to go to the info I wanted to learn about. | Strongly Disagree (1) Disagree (2) Somewhat Disagree (3) Somewhat agree (4) Agree (5) Strongly Agree (6) |
| These videos were easy to understand. | Strongly Disagree (1) Disagree (2) Somewhat Disagree (3) Somewhat agree (4) Agree (5) Strongly Agree (6) |
| This education helped me easily understand what insulin does for my diabetes. | Strongly Disagree (1) Disagree (2) Somewhat Disagree (3) Somewhat agree (4) Agree (5) Strongly Agree (6) |
| I am confident that I can use this website/system to access to the information I need to manage my diabetes. | Strongly Disagree (1) Disagree (2) Somewhat Disagree (3) Somewhat agree (4) Agree (5) Strongly Agree (6) |
| It was helpful to have this education in a video format that I can watch anytime. | Strongly Disagree (1) Disagree (2) Somewhat Disagree (3) Somewhat agree (4) Agree (5) Strongly Agree (6) |
| How likely are you to recommend these videos to your colleagues? | |
| What would you need to feel more comfortable in: a) Your own decision-making regarding recommending the influenza vaccination to patients with chronic disease, including diabetes | Free form text |
| I would recommend this education to any patient who is new to insulin. | Strongly Disagree (1) Disagree (2) Somewhat Disagree (3) Somewhat agree (4) Agree (5) Strongly Agree (6) |
| What would you need to feel more comfortable in: b) Convincing your HCPs colleagues regarding recommending the influenza vaccination to patients with chronic disease, including diabetes | Free form text |
| What would you need to feel more comfortable in: c) Additional information to help you convince your patients with chronic illness, including diabetes to accept influenza vaccination | Free form text |
| How satisfied are you with the video content? | 1 to 5 scale (1 = very unsatisfied-5 = very satisfied) |
| Do you think the videos addressed key concerns raised by patients? | 1 to 5 scale (1 = not at all-5 = very much) |

TABLE 1-continued

| Please indicate your profession | General Practitioner, Specialist physician, Nurse, Other, please specify |
|---|---|
| Is there anything would you change about the videos? | Free form text |
| I feel more confident taking my insulin having watched these videos | Strongly Disagree (1) Disagree (2) Somewhat Disagree (3) Somewhat agree (4) Agree (5) Strongly Agree (6) |
| This education helped reduce anxiety I had about taking insulin. | Strongly Disagree (1) Disagree (2) Somewhat Disagree (3) Somewhat agree (4) Agree (5) Strongly Agree (6) |
| Do you intend to receive your influenza vaccine this influenza season? | Yes (1) No (0) |
| This education helped me better understand how I can control my diabetes using insulin. | Strongly Disagree (1) Disagree (2) Somewhat Disagree (3) Somewhat agree (4) Agree (5) Strongly Agree (6) |
| This education helped me better understand how to give myself my insulin. | Strongly Disagree (1) Disagree (2) Somewhat Disagree (3) Somewhat agree (4) Agree (5) Strongly Agree (6) |
| This education helped me explain to my family, friends, and co-workers, important information about my condition or disease. | Strongly Disagree (1) Disagree (2) Somewhat Disagree (3) Somewhat agree (4) Agree (5) Strongly Agree (6) |
| This education helped me understand how to better communicate with my doctors and nurses. | Strongly Disagree (1) Disagree (2) Somewhat Disagree (3) Somewhat agree (4) Agree (5) Strongly Agree (6) |
| This education will help me make better food choices to manage my condition or disease. | Strongly Disagree (1) Disagree (2) Somewhat Disagree (3) Somewhat agree (4) Agree (5) Strongly Agree (6) |
| I personally related to this education (this information was representative of my experience). | Strongly Disagree (1) Disagree (2) Somewhat Disagree (3) Somewhat agree (4) Agree (5) Strongly Agree (6) |

(3) Content Viewership data. For example, if the patient is a returning patient, how many of the videos assigned to the patient for the patient's education did the patient watch? Did the patient skip any particular videos which are statistically linked to patient behavior or diagnosis?

(4) Demographic and self-reported data. The system can prepare a score, for use in the weighted equation to determine activation level, which is based on the demographic data provided by the patient. Exemplary demographic data can include race, gender, education, career, family size, salary, geographic location, military background, hobbies, etc.

(5) Medications currently prescribed, and the patient's pattern in taking those medications.

(6) Co-morbidities, that is, the patients concurrent disease conditions that are being treated simultaneous, i.e. patient may have both heart failure and be a type 2 diabetes patient who is using insulin (7) Online viewing habits. For example, what websites the patient visits, how often, times of day, etc. For example, online retailers can often develop a profile of an individual based on the individual's searches on the Internet, likes on Facebook, videos watched, content of email messages, etc. If a patient were to give permission for similar access, the system disclosed herein can use such information to develop additional data points and references in evaluating the patient and his/her activation level. It should be emphasized that such information would only be collected with the patient's explicit permission and knowledge.

(8) Real-time behavior of the patient based on video and voice recordings. For example, the patient can begin filling out a survey or healthcare questionnaire (such as that described above). While the patient is completing the survey, a camera can be recording the user behavior. Alternatively, a microphone can capture a patient verbally answering one or more of the survey questions. A "smart home speaker" can also be programmed to greet the patient at the same time every day with prompts to the survey. For example, in one configuration, the camera can record facial expressions of the patient (frowning, furrowed brow, etc.). In another configuration, the camera can record movements of appendages such as arms and legs, turning of the head, leaning, fidgeting, yawning, etc. The system can also identify time periods between repeated occurrences. These time periods can be used to identify additional behaviors of the patient. For example, multiple yawns within a two minute period can indicate the patient is tired, smiling then looking away may indicate shyness or pretending to like a circumstance, etc. These various behaviors are recorded, identified, and can then be used to calculate one or more scores.

All of these data points, or some of these data points, can be relied upon in analyzing a patient. In collecting these data points, it is noted that this data relies on real-time collections of data, and generating a score based on the real-time collected data. At run-time, no analysis of large data sets is being performed, such as an analysis on historical claims data.

These data inputs are collected, weighted, and applied to a machine learning algorithm. The machine learning algorithm extracts higher order knowledge about the patient from the data being collected in real time. More specifically, the disclosed systems rely on patient reported outcomes (i.e., the patients provide information about their condition, symptoms, responses to specific situations and whether expectations were met in various contexts, and the patient's attitudes towards their self-care, instructions received, compliance, adherence, as well as towards their disease, diagnosis, and treatments. By gathering this information, the system can also make determinations regarding the patient's perceived stigma's and level of motivation.

Based on the activation level, behavioral profile, and/or behavioral phenotype obtained, patients can be classified/segmented into distinct categories, and can receive healthcare based on that segmentation. For example, if a patient is categorized as likely to understand a diagnosis a relatively short doctor visit can be scheduled, whereas is the patient is categorized as unlikely to understand the diagnosis the scheduled visit can be longer. Likewise, if additional care is needed with a specific aspect of the patient's care (i.e., a concern with needles associated with insulin), adjustments can be made to reflect that extra care. In this manner, the patients can be classified into distinct risk pools which categorize the healthcare utilization, adherence, and health trajectory of the patient, and this is based on their behavioral phenotype, not traditional claims data.

The categories in which patients can be organized can vary based on demographics, understanding, diagnosis, behavior, etc. An exemplary list of such categories is illustrated in Table 2:

TABLE 2

1. To what extent are "Basic Needs Met - Social Determinants of Health"; take SDOH Survey and use it to validate the answers received and new SDOH questions created in Survey manager.
2 To what extent does the patient exhibit Bias, Stigma or Shame regarding their health condition or need for use of healthcare intervention
3. To what extent does patient feel self-empowered? Demonstrate Self Efficacy? Stanford Self Efficacy, The Patient Activation Measure and other Self Efficacy measures
4. To what extent is patient signifying distress? Diabetes Distress, Cardiac, Oncology measures and other distress indicators
5. To what extent does Patient exhibit Anxiety, Worry or Concern? PHQ2, Other Anxiety measures
6. To what extent does Patient exhibit signs of Depression? Becks Sleep and Depression Index; Depression questionnaire
6. To what extent does Patient clarify their own Quality of life expectations? KCCQ, Other QOL indicators
7. To what extent does patient exhibit executive functioning skills (ADD, ADHD Surveys)
8. Knowledge gap surveys created by Healthcare staff treating patients
9. How much unique content has the patient watched?
10. How much total content viewership?
11. How long have they been viewing?
12. How many distinct viewing sessions? Average content assets consumed in each viewing session
13. Medications and Comorbidities
14. Frequency of Prescription refill for last 12 months based on condition (Adherence patterns in the past)
15. Perceived Attentiveness of Clinician and Does my clinician like me
16. Patient Satisfaction/Ease of Use/Willingness to Refer
17. Usefulness of the content
18. Connection to the content and patient stories
19. Online engagement metrics
20. Feelings of Self Worth Furthermore, these categorizations and segmentations can allow the system to generate education tools and interventions which are specifically tooled to assist that individual patient based on that patient's behavioral phenotype and health score. More specifically, based on the activation level generated for the patient, the diagnosis of the patient, the patient's pattern of completing assignments (i.e., taking medicine, watching videos, read educational materials, etc.), and/or other information (including demographics, activation levels and other data which may be used in generating the behavioral phenotype), the system can generate a library of videos for the patient to watch which will aid in the self-management of their recovery or disease management. To date, clinical research is already proving the benefits of this custom library with respect to Cardiac and Diabetes patients, and it is anticipated that similar benefits will be found in other aspects of healthcare. In a preferred configuration, the library of videos would incorporate microlearning, where each video is between 15 seconds and 3 minutes long, where the videos selected (and the order of the videos) are selected based on the specific data associated with that patient. In some configurations, the videos are pre-recorded to specific lengths, then selected for inclusion into the libraries of specific patients. In other configurations, the system can edit a longer video to the desired length and content required for a patient, then place the edited version of the video into the patient's library.

The microlearning can be used to augment, or improve, on the self-learning the patient needs to do to be informed enough to adequately take their medications, follow instructions, and otherwise improve their health. To that end, a variety of supervised learning, machine learning, and/or neural net algorithms can be used to provide patients with the best materials for their particular circumstances.

For example, to enable machine learning, training data sets can be collected which describe relationships between patients, their health risk levels, and their probable future trajectory without intervention (i.e., if they do not receive any medical advice or treatment). The data associated with the patient, such as the patient's demographic data, activation level, history within the system (i.e., if they are a returning patient, did they watch all of the last videos prepared for them? If not, which videos did they watch?). This data can be used to predict, via the machine learning algorithm, the patient's ability to succeed at managing their condition when they return to the healthcare facility. When the patient returns and quantifiable data can be obtained about the patient's self-management of their condition, that updated "current" data regarding the patient is automatically fed into the database, the machine learning algorithm "learns" more about the patient, and the machine learning algorithm updates it's patient education recommendations for that patient based on that information.

Consider the following scenario. A new patient arrives and is scheduled for a head scan. Before arriving, the patient fills out an online questionnaire regarding basic/generic demographic information (i.e., weight, height, race, gender, age, education, address, etc.) as well as illness specific data (i.e., depression, anxiety, autism, flu, intestinal issues, ocular issues, cardiac issues, etc.). In some configurations, a camera can identify the patient and make determinations about the patient based on video analysis of the patient. For example, if the patient is visually identified as obese, anorexic, moving too slow (or below a threshold rate), moving too fast, having odd or awkward movements, having an unhealthy skin tone, etc., that patient-specific data can be recorded and added to the patient data. Based on this collected data, the system can generate (1) an initial activation level for the patient based on the data provided, and/or (2) an initial behavioral phenotype.

The behavorial phenotype or individual behavioral profile can be used to allocate resources for the patient's care, and can further be used to determine how ready the patient is to receive instructions, medications, treatments, etc. For example, a default visit time for a doctor with a patient may be fifty minutes. Based on the engagement patterns and overall behavioral phenotype, the duration of the visit time can be adjusted to better serve the patient by shortening or increasing their appointment times. Exemplary adjustments can include: appropriate appointment times with the right level of care, the providers to be seen, series of alerts and notifications so that those that most need monitoring are being monitored at the right levels, and the right set of self-management microlearning content such that patients can course correct or better enable the patient to more successfully self-manage their healthcare after the visit. Those with the highest or riskiest scores may move to the top of the list for personal attention and those that are lower risk or highly activated might receive more appropriate resourcing such as text based guidance or phone call guidance versus waiting unnecessarily in a waiting room for their standard appointment. This patient triage approach is a direct result of the machine learning algorithms and the data collected on the patient through patient reported sources as well as observation.

The microlearning content can include videos which are selected and/or tailored to the patient based on their diagnosis, their activation score, their pattern of behavior from previous interactions/prescriptions/assignments, and machine learning algorithms. The machine learning, at a basic level, can adjust weighted factors based on simple linear regression and complex regression analyses. With each iteration, an additional regression analysis on the factors can be performed and, when the additional regression analysis indicates a distinct weighting should take place, the factors are adjusted based on the additional regression analysis. The machine learning can further incorporate neural networks as well as deep neural networks (an artificial neural network containing more than one hidden layer, or more than one layer of non-linear relationships). The different scores can be regressed on each intervention model, and can be regressed again based on content viewership data variables, to provide a truer picture of the patient's expected activity and adherence level.

In addition using path analysis of customized, tailored patient education instructional content, and most relevant communications and messages, the system is able to predict longitudinal activation and adherence, and then provide, in real-time, the right solution (healthcare intervention for that condition or that patient).

For example, over time multiple patients diagnosed with a disease may be assigned to view microlearning videos associated with that disease. The machine learning algorithm determines which video segments are assigned to each patient's customized video library, then receives feedback about which videos the patient actually watched and the patient's overall self-care. Based on the improvements to each patient, which videos were seen, etc., the machine learning algorithm can determine which videos are working to improve the patient's health and which are not, then customize videos for that disease based on that feedback. Similarly, the videos can be customized to specific demographics, stages of disease, treating doctor, etc.

In other words, the system can predict the likelihood of patient health trajectory as managed (predicted) by the patient given their particular health behavior trajectory from the aforementioned inputs, and then suggest the right level of management. For example, the system can predict the likelihood that Type 2 diabetes patients who are using insulin will not adequately manage their glucose levels. Moreover, the prediction can have additional levels of detail, such as predicting that the patient's A1C levels will not go down or be controlled, that the patient will spend more time unnecessarily in Hypo or Hyper glycemic states, and that this lack of good management will then cause them to excessively use the healthcare system (when it could have been prevented with appropriate interventions). Similar predictions can be made for other diseases and patient conditions. In addition to patient classification, the system can also predict the number of patients in a hospital or clinic setting that will fall into low to high risk categories and the different levels of interventions which are best prescribed to those patients. Finally, beyond prediction and classification, the system can provide the patient with the right intervention, personalized to their needs or their behavioral phenotype to achieve the best outcome possible, as determined by the machine learning algorithm and the analyses.

FIG. 1 illustrates an exemplary flow chart relating patient actions to system performance. In this example, the focus is on a patient being admitted to the hospital. In other configurations, a patient can be given the same behavior experience profile questionnaires at home, pre-arrival, or post discharge but outside the hospital. Here, a patient 102 arrives at a healthcare facility 106, and begins filling out a questionnaire 108. In many configurations, the patient 102 can fill out the questionnaire 108 online using a mobile device, tablet, laptop, or other computing device. A system 104 configured as described herein receives the answers of the questionnaire 110 and determines a patient behavioral profile 112. In some cases, the system 104 can also receive, from a database, a history of the patient, such as previous diagnoses, compliance with instruction, etc. In determining the patient behavioral profile 112, the system 104 can utilize machine learning, neural nets, or any similar form of iterative improvement software, where the software is improved to be capable of making improved predictions at regular intervals. Exemplary iteration intervals can include modifying the software based on a defined threshold number of patients being seen and reviewed, based on a predetermined amount of time passing, or based on drops in prediction efficiency.

The system 104 then recommends healthcare resource allocations 114 (such as type of clinician, the appropriate amount of time spent with the doctor, nurses, education materials, approach, type and specific messages, etc.) based on the behavior profile consisting of a series of weighted factors ranging from patient activation levels, attitudes, bias, knowledge (gaps), online activity and other weighted factors. The patient meets with the doctor 116, at which point additional resources are allocated based on the patient's behavior profile and their health record. 120. In addition, the system 104 generates a microlearning library 124 for the patient based on the patient being cared for in that particular healthcare system facility, the patient's activation level, the diagnosis, demographics, individual behavior, the patient's behavior profile, and/or other factors. This microlearning library can, for example, include videos of fifteen seconds duration to three minutes duration, and/or other materials designed to be consumed within a similar timeframe, which follow the principles of microlearning i.e. embedding cognitive science, behavior science, and realism. Which videos are selected, or which portions of videos are selected, can be determined by the machine learning algorithm. In one example configuration, a video repository contains many different versions of videos explaining a certain topic, and the machine learning algorithm determines which version would be most applicable to the patient. In another configuration, the video repository contains only a single version of each video, however, the video is tagged with metadata indicating distinct portions within the video. When generating a custom, or tailored, video library in this configuration, the machine learning algorithm can identify the video and the specific portions of the video which would best serve the current patient, then prepare an edited version of the video containing those portions. In this manner, not only the video, but the specific content of the video, is customized to the patient.

The patient then watches the videos within the microlearning library 126, and a record of which videos the patient watches 128 is made within the system 104. This data is then used to iteratively update the machine learning algorithm 130. If, for example, the system 104 identifies that viewers who watch a specific video, or a portion of a video, have better results than those who do not view the video, the system 104 can begin identifying what specific portion of that video is conveying those results. Likewise, the system can compare the viewing habits of individuals with their results on a subsequent visit or, if the system has mechanisms in place to record patient behavior during self-care, can make correlations between the individual's behavior and the results, then make self-care recommendations to the patient and other patients based on those correlations. Comparisons are made between patient visits, within and to demographics, healthcare systems, zip codes, patients with similar diagnoses, similar and different behavior phenotypes and disease conditions and other factors.

Figure 2:
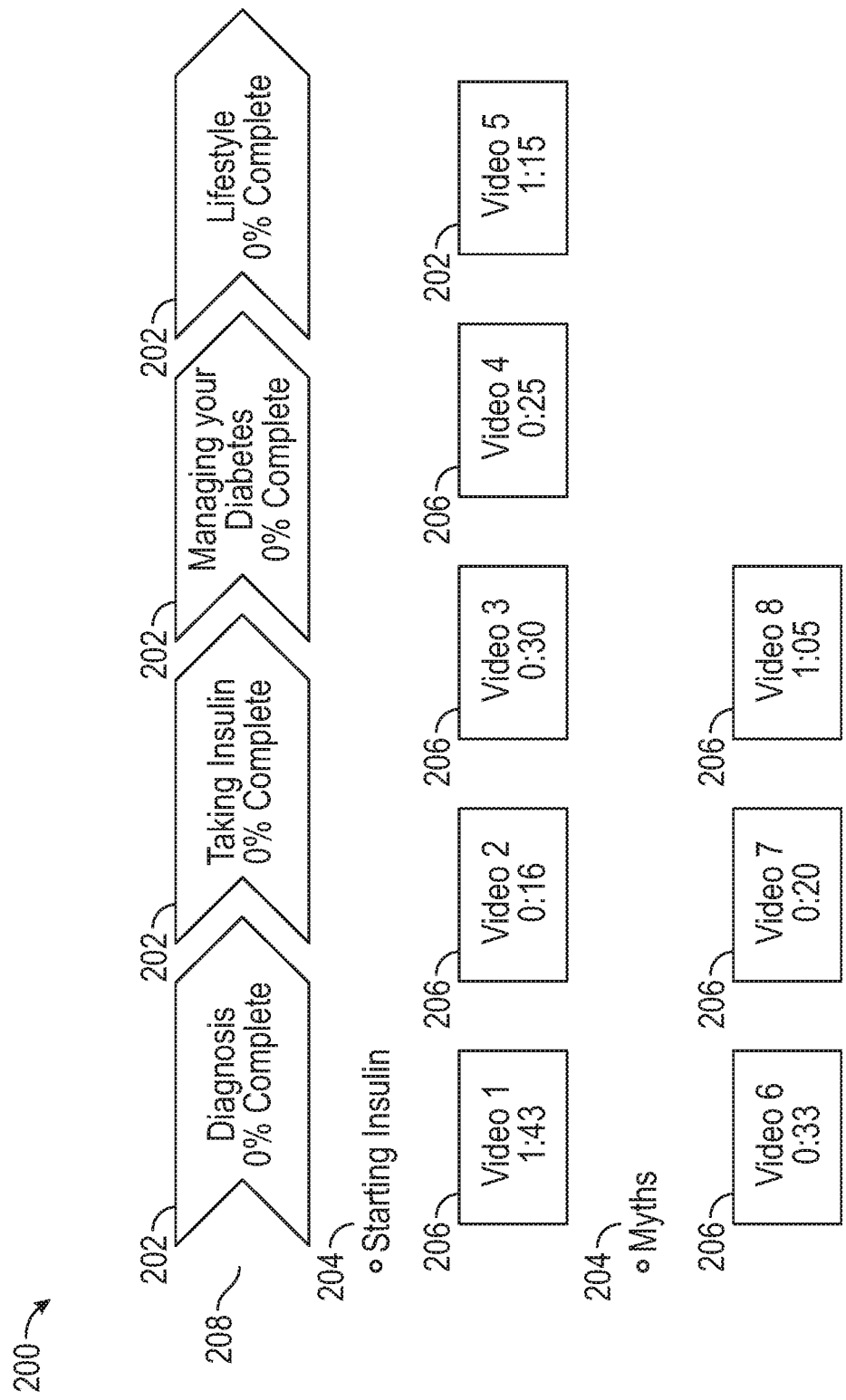
FIG. 2 illustrates an exemplary user interface for accessing the tailored video library.

FIG. 2 illustrates an exemplary user interface 200 for accessing the tailored video library. In this example 200, the patient is provided with a ribbon 208 illustrating different sections 202 of education which the patient needs. For this particular patient learning how to manage diabetes, there are four different sections 202. Within each section, there can be subgroups 204 of videos 206 which are presented to the user. Each video 206 can be selected, modified, and otherwise edited by the machine learning algorithm as required.

Figure 3:
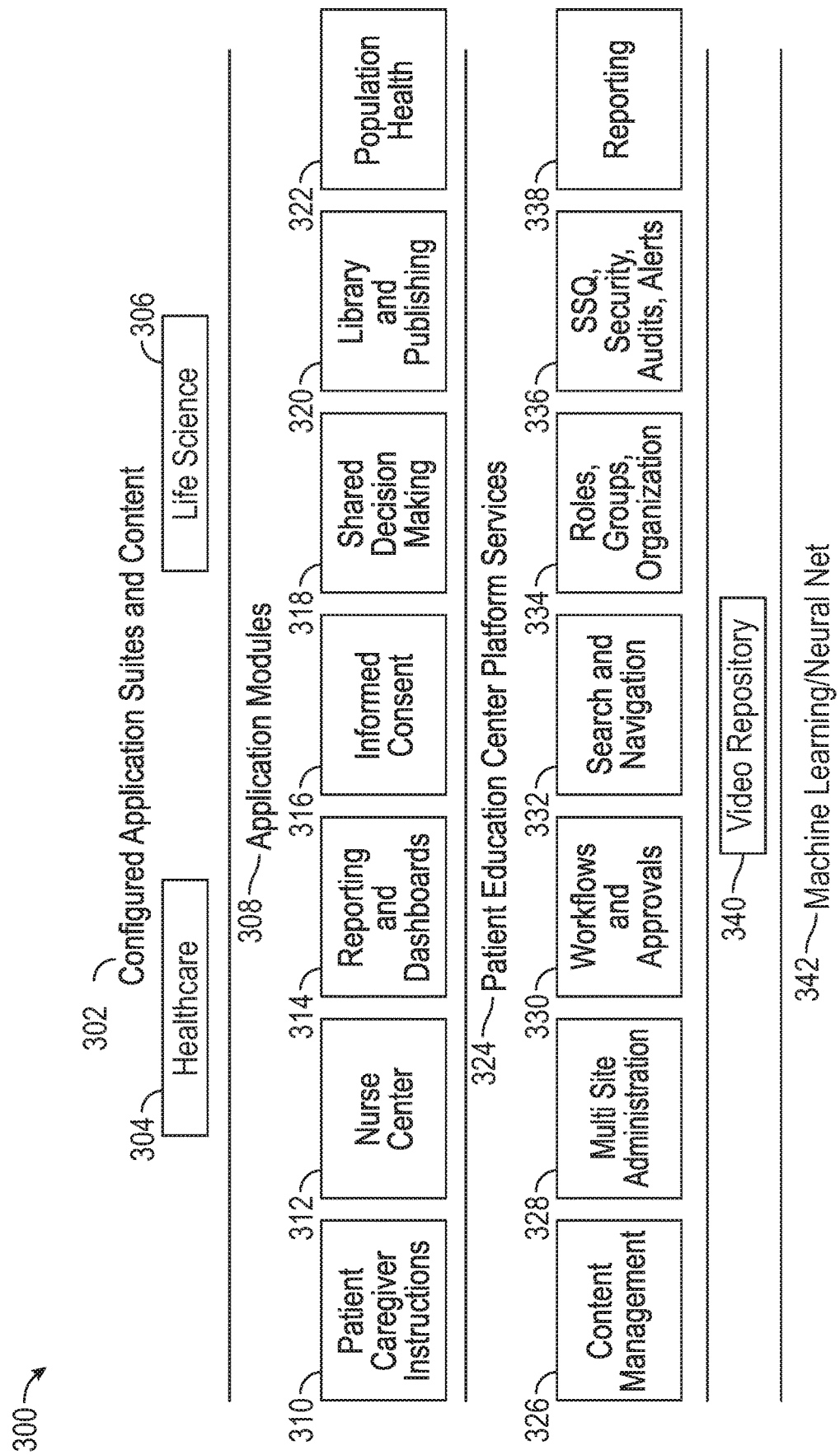
FIG. 3 illustrates an exemplary system architecture.

FIG. 3 illustrates an exemplary system architecture 300. In this example, the architecture 300 is divided into five sections: the configured application suites and content 302, the application modules 308, the patient education center platform services 324, the video repository 340, and the machine learning/neural net algorithms.

Exemplary applications suites and content 302 to which the principles disclosed herein can be applied include healthcare 304 applications and life sciences 306 applications. In particular, applications where clinically validated questionnaires can be used to predict the condition of a patient, and where the patient's likelihood of following instructions can be predicted.

Exemplary application modules 308 are specific facets, or areas, of the application suites 302. For example, as illustrated, in dealing with healthcare 304, exemplary modules can include patient and caregiver instructions 310 (this module is the patient facing set of playlists which are tailored to a given disease state), a nurse center 312 (this module allows nurses to invite patients to log into the system with their own credentials, which allows the system to be a "standalone portal" independent of any EM/scheduling system integration), reporting and dashboards 314 (this module allows administrators to view metrics on patient viewership and all of the other data mentioned herein and for the health system to view an aggregate view of all patients in a specific population of patients by region, disease progression), and to view outcomes against these populations over time. Informed consent 316 (this module allows providers to obtain signature from a patient prior to enrolling them in a clinical trial or performing a procedure and provides them with risks and benefits of the procedure), shared decision making 318 (this module allows the patient and clinician to determine the appropriate course of treatment), library and publishing 320 (this module allows providers to manage their content via a central repository, while enabling customization and versioning of content by hospital & service line), and Communication and outreach 322 (this module allows for the health system to communicate with the patient, deliver surveys via text and email, to collect the patient generated health data and patient reported outcomes from individual patients, to bring that data back into the model for the machine learning to further refine the model, and for the patient to gain better resources by generating insights using claims or EMR data only. This module can also integrate with a care coordination planning system, and is not a care coordination system).

Exemplary patient education center platform services 324 are those areas specifically available to the patient to assist in their education. This can include content management 326, multi-site administration 328, workflows and approvals 330, search and navigation 332, roles/groups/organizations 334, SSQ/security/audits and alerts 336, and reporting 338. These platform services 324 are how the patient interacts with the system, and how content/solutions are provided to the patient.

The video repository 340 is the database, or storage systems, where the system videos are maintained. In addition, this video repository 340 can include the Internet, cloud computing, or other distribution systems through which the content is delivered to the patients.

The machine learning/neural net 342 aspect of the system architecture 300 can be contained within a server, a computing device (such as a laptop, desktop, or other tangible computing device), or can be distributed over multiple servers as a cloud architecture. In some configurations, the machine learning can be provided by a third party service, such as "Amazon Machine Learning" by Amazon Web Services (AWS)®, or other similar products.

Figure 4:
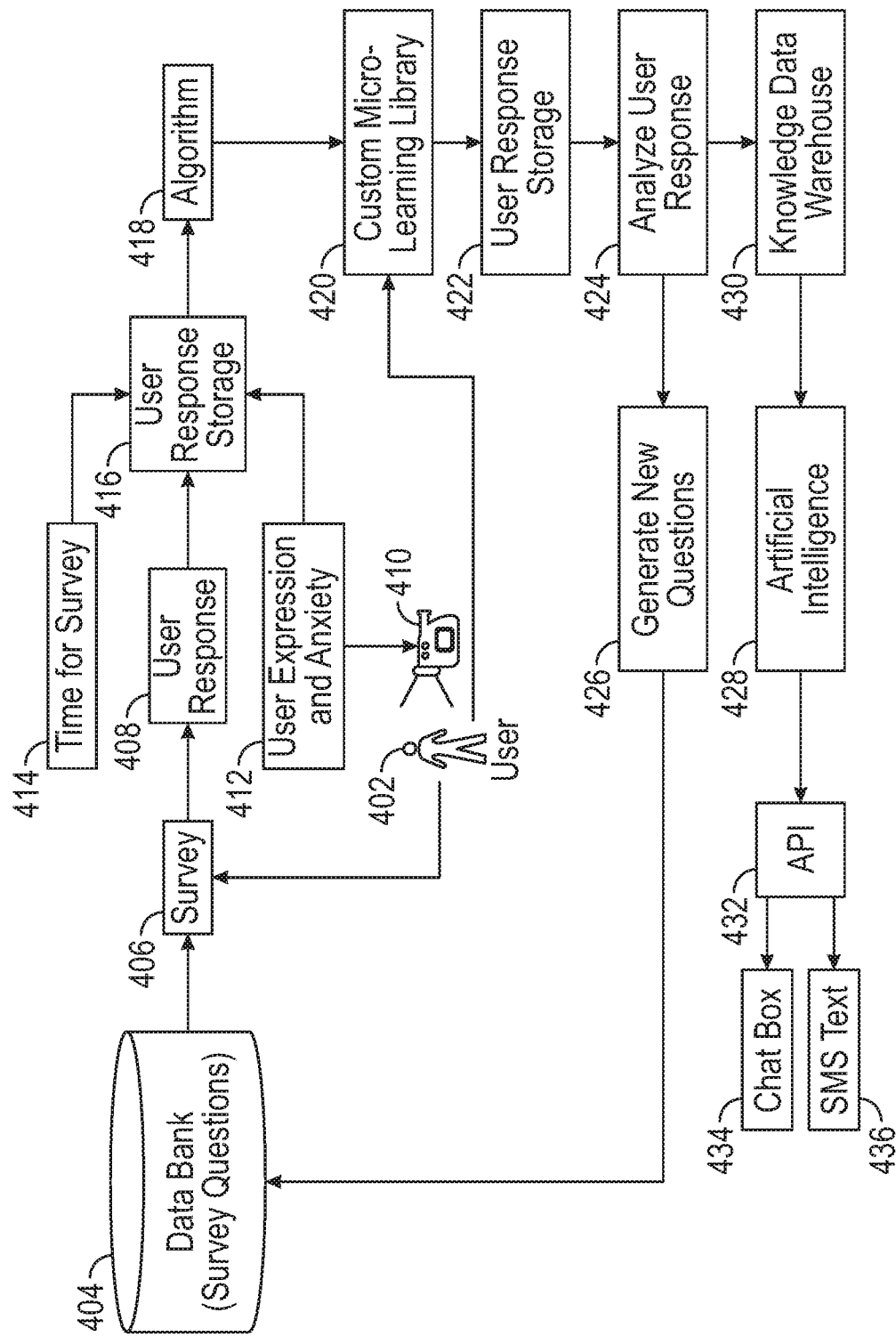
FIG. 4 illustrates an example of a user interacting with the system.

FIG. 4 illustrates an example of a user 402 interacting with the system. In this example, the user 402 takes a survey 406 generated by the system using a data bank 404. The data bank 404 can contain previously generated survey questions, or can contain information which can be used to generate new survey questions. The user 402 completes the survey 406, to create a user response 408. In this example, a camera 410 records the user 402 completing the survey, and records information regarding the user's 402 behavior, expressions, etc., to create recorded information regarding the user's expression and anxiety 412. In this example, the time required for the user 402 to complete the survey 414 is also recorded. The time for the survey 414, the user response 408, and the user expression and anxiety 412 are all recorded in a user response storage 416. This stored data is then fed as input into an algorithm 418, which weighs respective elements of the user's stored data.

In some instances, such as the first time the user 402 goes to visit a new doctor, the only information which may be fed to the algorithm 418 is the information gathered as the user is filling out the questionnaire (such as the time for the survey 414, the user response 408, and the user expression and anxiety information 412). However, in instances where the user 402 is a repeat visitor, information associated with previous visits of the user 402 can be used in the algorithm. Additional information which can be used as inputs into the algorithm 418 include information regarding how the user 402 responds to suggestions, prescriptions, presented materials, etc., as well as diagnoses.

The algorithm 418 generates a score which can be used to generate a custom library of videos, or a "custom microlearning library" 420. In some configurations, the score can be one-dimensional, such as a number score ("65", "89", etc.) or a letter score ("A", "B", "C", etc.) is used to generate a custom microlearning library 420 of videos for the user 402 to watch. In other configurations, the score can be multi-dimensional, such as "C-75" or "D-16". In these multi-dimensional scores, one dimension (in this example, the letter) can be used for a particular diagnosis, and another dimension (in this example, the number) can be used for a particular level, or group, of videos associated with the diagnosis. Thus, "C-75" may indicate a particular, custom set of Cardiac related videos, and "D-16" may indicate a particular, custom set of Diabetes related videos.

As the user 402 watches and interacts with the videos, data about the user behavior is recorded in the user response storage 422. In some configurations, this can be the same user response storage 416 used for storage of the survey questions, or can be a distinct storage unit. The system analyzes the user responses 424 stored, and can use that analysis to generate new questions 426 or information which can be added to the data bank 404. In addition, Artificial Intelligence 428 (A.I.) can be deployed to generate the new questions 426, where the A.I. uses a knowledge data warehouse 430 (such as information shared between doctor's offices, hospitals, etc.) to generate questions. The A.I. 428 can also interact with users via chatbots 434 and text messages 436 by interacting with an API 432 (Application Programming Interface).

In this manner, the system continues to improve itself, providing a better customized library of videos 420 to the user 402 with each iteration/interaction.

Figure 5:
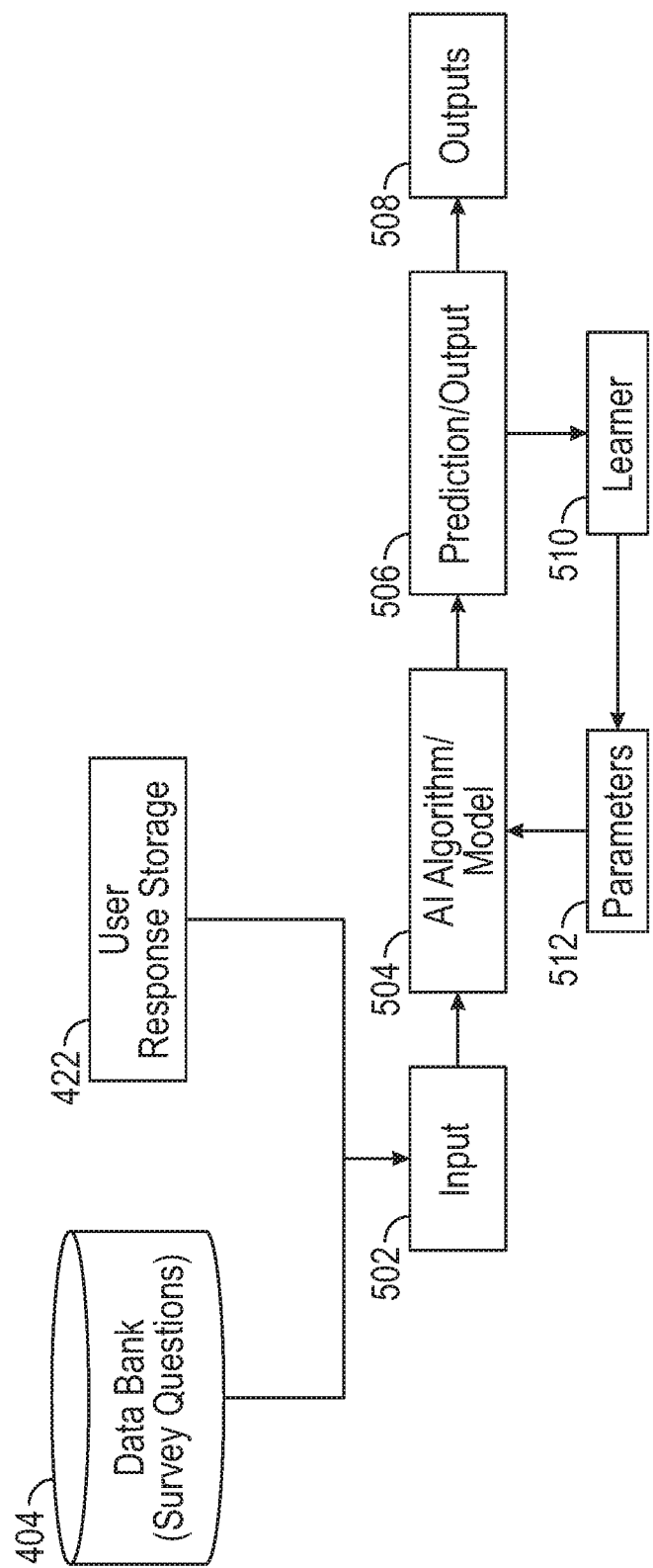
FIG. 5 illustrates an example of the machine learning process deployed by the system.

FIG. 5 illustrates an example of the machine learning process deployed by system. In this example, the data bank 404 and the user response storage 422 of FIG. 4 are used as inputs 502 to the machine learning system. The system deploys an A.I. Algorithm/Model 504, which evaluates the current inputs 502 to the system and generates a prediction/output 506. These predictions 506 can be output 508 for use in generating new questions, modifying the algorithm 418, changing how videos are selected, combined, modified, etc. The prediction/output 506 is also provided to a learner 510, which identifies if predictions made actually come to pass. For example, if it is predicted that a user will watch certain videos and not others, the learner 510 will track the prediction and the resulting reality. Based on the comparison between the prediction and reality, a parameter 512 (or more) of the A.I. algorithm/model 504 will be changed, meaning that the actual code being used to evaluate the inputs 502 will be modified according to the parameter 512. In this manner, the code used to evaluate, learn, and predict the user's behavior is being iteratively modified in a particular way.

Figure 6:
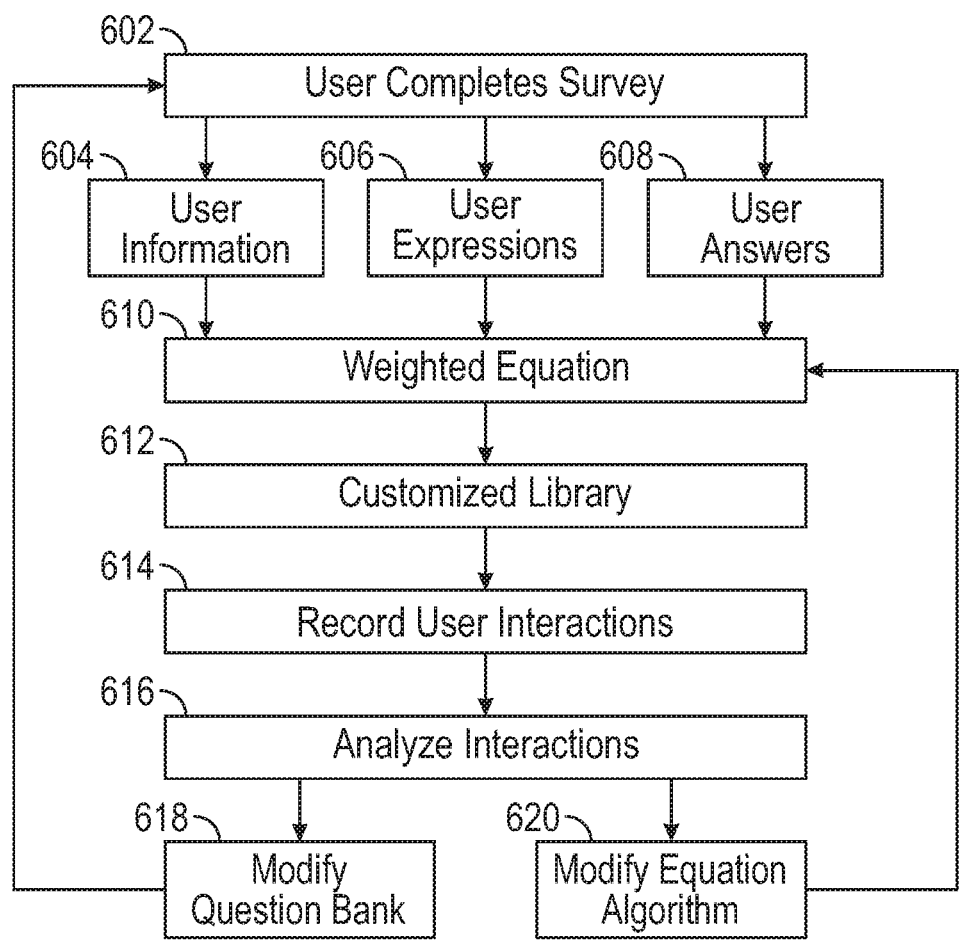
FIG. 6 illustrates an example method embodiment.

FIG. 6 illustrates an example method embodiment. In this example, the user completes a survey (602), which generates the user answers (608). Also present can be user information (604), such as demographics of the user, socioeconomic data about the user, survey answers provided in previous visits, previous predictions, user behavior (such as information regarding which videos were watched and how much of each video was watched), etc. User expressions 606 information (such as user behavior captured by a camera and identified using facial recognition or behavioral recognition software) can also be present 606.

This information 604, 606, 608 is used by an algorithm to form a weighted equation (610), where the different factors, answers, or conclusions based on the answers can be weighted, then combined to form a score associated with the user. For example, part of a score calculation can be: Score=((Self Efficacy Weight)×(Self Efficacy Score))+(Knowledge Questions Score)+((Attitude Towards Insulin Weight)×(Attitude Towards Insulin))+((Depression Weight)×(Depression Score))+((Anxiety Weight)×(Anxiety Score)) . . . .

The various scores can be based on the individual user's responses, both present and past (when available). The various weights can be individually determined based on past behavior of an individual, or can be based on group behaviors. The final score generated, the "Behavioral Profile Score", can then be used to generate a customized library (612) of videos, a customized communication and outreach strategy and additional custom questions based on previous answers. In some cases, these videos can be "microlearning" videos which are selected specifically based on the scores, answers, and behaviors of the user. Similarly, in some cases, these videos can be cut, spliced, or modified based on the scores, answers, and behaviors of the user. Once the user has the custom library available, the system then records user interactions (614) with the library. For example, does the user watch all of the videos? Does the user start the video, then stop it before it concludes? Does the user watch the videos in order?

The recorded interaction information is then analyzed (616), and the system can modify the question bank (618), such that the user (or a different user) could receive distinct questions in the future. In addition, the system can modify the weighted equation algorithm (620), such that which videos, or which portions of videos, would be presented to a similar user in the future can change.

Consider another exemplary method embodiment. In this example, the method can include: receiving, from a mobile device, answers to a healthcare questionnaire, wherein the answers are received in real-time as a patient completes the healthcare questionnaire on the mobile device; generating, via a processor and based on the answers, at least one clinically validated health score; recording a video of the patient as the answers are completed; identifying, via the processor and based on the video, at least one expression of the patient made during completion of the healthcare questionnaire; calculating a score of the patient based upon the answers and the at least one expression; receiving a diagnosis of the patient; and generating a library of videos customized to the patient based upon at least (1) the score and (2) the diagnosis.

In such an example, the video of the patient can capture at least one of facial expressions made while completing the healthcare questionnaire and body posture while completing the healthcare questionnaire.

In such an example, the library of videos can be customized to the patient by: identifying a plurality of portions corresponding to a plurality of videos, each portion in the plurality of portions being a video segment identified as relevant to the patient based upon the score and the diagnosis; and caching the plurality of portions within a memory cache distinct from that of the plurality of videos, to yield the library of videos.

In such an example, the method can be further augmented to include, as the patient watches videos within the library of videos: recording content viewership data regarding how patients view the library of videos; generating, by weighting at least: one clinically validated health score, the score of the patient, demographic data associated with the patient, and the content viewership data, an activation score of the patient; allocating additional resources, via a machine learning algorithm, for the patient based on the activation score; receiving data indicating portions of the library of videos watched by the patient, to yield viewing data; receiving online data identifying online behavior of the patient; and updating the machine learning algorithm based on the viewing data and the online data. These additional resources can include additional videos being added to the library of videos. In addition, such a method can include generating, via an updated machine learning algorithm, a modified healthcare questionnaire for use in future patient interactions. Likewise, in such a method, the activation score of the patient can be further based on how accurately the patient follows prescribed behavior.

In another example, the method of FIG. 6 can be augmented to further include: recording audio of the patient as the answers are completed, where the identifying of the at least one expression of the patient made during completion of the behavioral questionnaire is further based on the audio of the patient. For example, the system can use audio captured while the patient completes the behavioral questionnaire to make additional determinations about the expression of the patient. If, for example, the patient signs or sounds exasperated, the system can combine the audio of that sigh with other gesture or behavior data captured by the video, then use that data to make additional determinations about the mental or physical state of the patient.

Figure 7:
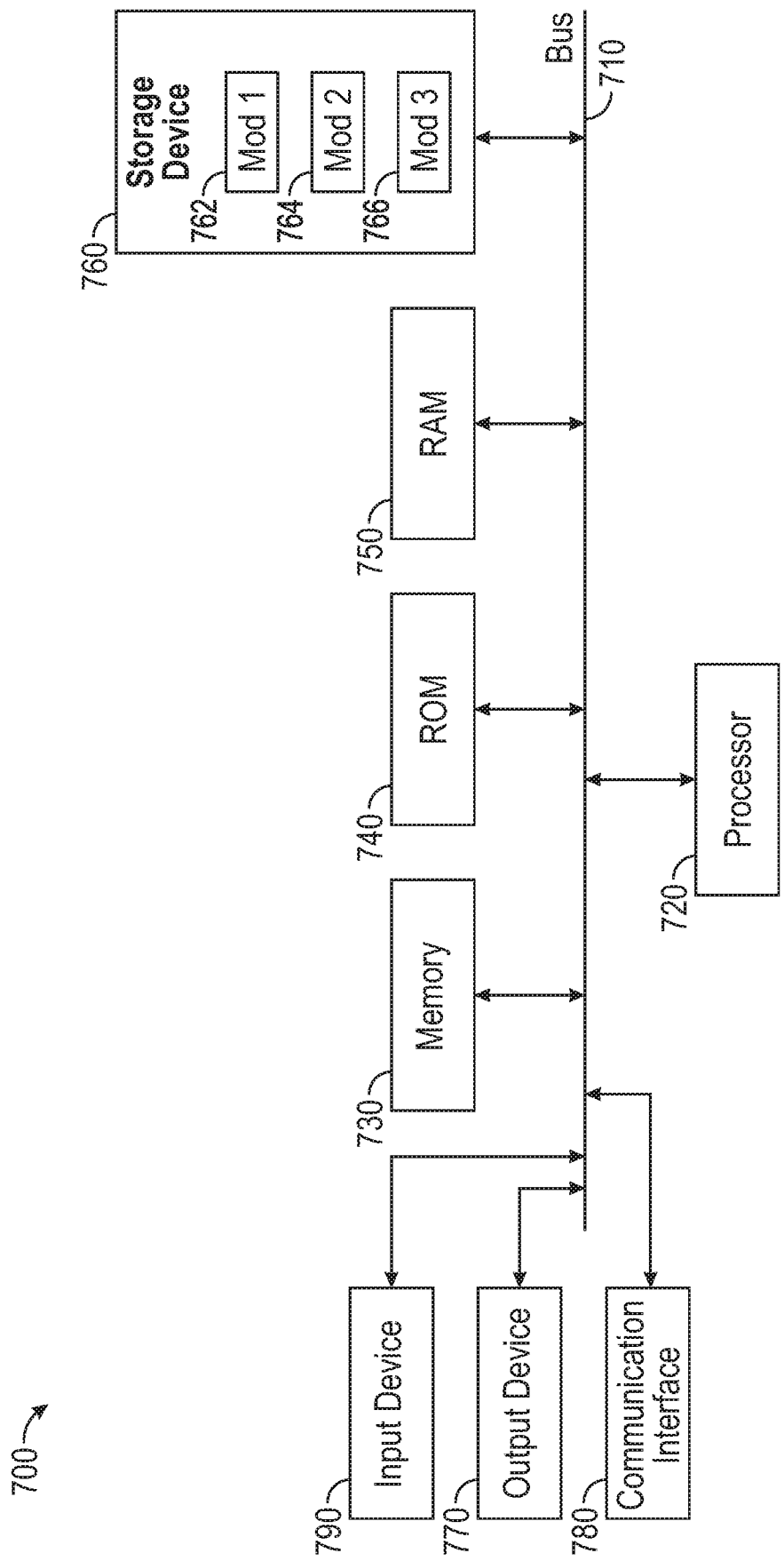
FIG. 7 illustrates an exemplary computer system.

With reference to FIG. 7, an exemplary system 700 includes a general-purpose computing device 700, including a processing unit (CPU or processor) 720 and a system bus 710 that couples various system components including the system memory 730 such as read only memory (ROM) 740 and random access memory (RAM) 750 to the processor 720. The system 700 can include a cache of high speed memory connected directly with, in close proximity to, or integrated as part of the processor 720. The system 700 copies data from the memory 730 and/or the storage device 760 to the cache for quick access by the processor 720. In this way, the cache provides a performance boost that avoids processor 720 delays while waiting for data. These and other modules can control or be configured to control the processor 720 to perform various actions. Other system memory 730 may be available for use as well. The memory 730 can include multiple different types of memory with different performance characteristics. It can be appreciated that the disclosure may operate on a computing device 700 with more than one processor 720 or on a group or cluster of computing devices networked together to provide greater processing capability. The processor 720 can include any general purpose processor and a hardware module or software module, such as module 1 762, module 2 764, and module 3 766 stored in storage device 760, configured to control the processor 720 as well as a special-purpose processor where software instructions are incorporated into the actual processor design. The processor 720 may essentially be a completely self-contained computing system, containing multiple cores or processors, a bus, memory controller, cache, etc. A multi-core processor may be symmetric or asymmetric.

The system bus 710 may be any of several types of bus structures including a memory bus or memory controller, a peripheral bus, and a local bus using any of a variety of bus architectures. A basic input/output (BIOS) stored in ROM 740 or the like, may provide the basic routine that helps to transfer information between elements within the computing device 700, such as during start-up. The computing device 700 further includes storage devices 760 such as a hard disk drive, a magnetic disk drive, an optical disk drive, tape drive or the like. The storage device 760 can include software modules 762, 764, 766 for controlling the processor 720. Other hardware or software modules are contemplated. The storage device 760 is connected to the system bus 710 by a drive interface. The drives and the associated computer-readable storage media provide nonvolatile storage of computer-readable instructions, data structures, program modules and other data for the computing device 700. In one aspect, a hardware module that performs a particular function includes the software component stored in a tangible computer-readable storage medium in connection with the necessary hardware components, such as the processor 720, bus 710, display 770, and so forth, to carry out the function. In another aspect, the system can use a processor and computer-readable storage medium to store instructions which, when executed by the processor, cause the processor to perform a method or other specific actions. The basic components and appropriate variations are contemplated depending on the type of device, such as whether the device 700 is a small, handheld computing device, a desktop computer, or a computer server.

Although the exemplary embodiment described herein employs the hard disk 760, other types of computer-readable media which can store data that are accessible by a computer, such as magnetic cassettes, flash memory cards, digital versatile disks, cartridges, random access memories (RAMs) 750, and read only memory (ROM) 740, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 700, an input device 790 represents any number of input mechanisms, such as a microphone for speech, a touch-sensitive screen for gesture or graphical input, keyboard, mouse, motion input, speech and so forth. An output device 770 can also be one or more of a number of output mechanisms known to those of skill in the art. In some instances, multimodal systems enable a user to provide multiple types of input to communicate with the computing device 700. The communications interface 780 generally governs and manages the user input and system output. There is no restriction on operating on any particular hardware arrangement and therefore the basic features here may easily be substituted for improved hardware or firmware arrangements as they are developed.

The various embodiments described above are provided by way of illustration only and should not be construed to limit the scope of the disclosure. Various modifications and changes may be made to the principles described herein without following the example embodiments and applications illustrated and described herein, and without departing from the spirit and scope of the disclosure.

We claim:
1. A method comprising:
  receiving, at a computer system, training data sets describing relationships between: (1) patients diagnosed with a physical illness, (2) patient health risk levels, and (3) patient trajectories without intervention;
  training a neural network using the training data sets, resulting in a machine learning algorithm;
  receiving, at a processor from a mobile device, answers to a behavioral questionnaire, wherein the answers are received in real-time as a patient self-reports answers to the behavioral questionnaire on the mobile device;
  recording, via a camera, a video of the patient as the answers are completed;
  identifying, via the processor from the video of the patient, at least one facial expression of the patient made during completion of the behavioral questionnaire;
  identifying, via the processor from the video of the patient, at least one repeated body posture of the patient made during completion of the behavioral questionnaire;

calculating a time period between instances of the at least one repeated body posture;
calculating, via the processor, a numerical score of the patient based upon the answers to the behavioral questionnaire, the time period, the at least one repeated body posture, and the at least one facial expression of the patient made during completion of the behavioral questionnaire;
receiving, at the processor, a physical medical condition of the patient;
generating, via the processor executing a playlist algorithm using the physical medical condition of the patient and the numerical score, a playlist of videos associated with the physical medical condition;
receiving, at the computer system, a record of which videos within the playlist of videos were watched by the patient;
executing, via the computer system, the machine learning algorithm, with inputs to the machine learning algorithm comprising the record and outputs of the machine learning algorithm comprising a modification to the playlist algorithm; and
modifying, via the processor, the playlist algorithm according to the modification.

2. The method of claim 1, wherein the playlist of videos associated with the physical medical condition are customized to the patient by:
identifying a plurality of portions corresponding to a plurality of videos, each portion in the plurality of portions being a video segment identified as relevant to the patient based upon the numerical score and the physical medical condition; and
caching the plurality of portions within a memory cache distinct from that of the plurality of videos, to yield the playlist of videos.

3. The method of claim 1, wherein:
the training of the machine learning algorithm further comprises:
performing, via the processor, a regression on the training data sets, thereby identifying initial weights for the machine learning algorithm; and
as the patient watches videos within the playlist of videos:
recording content viewership data regarding at least one of how patients view the playlist of videos, type of content viewed, and recently viewed videos in the playlist of videos;
calculating an online engagement pattern for the patient based on the content viewership data;
generating, by weighting at least one of: a clinically validated behavior score, the numerical score of the patient, demographic data associated with the patient, and the content viewership data, a behavior profile score of the patient;
identifying additional resources for the patient based on the behavior profile score, the physical medical condition, and the online engagement pattern;
receiving data indicating portions of the playlist of videos watched by the patient, to yield viewing data;
receiving online data identifying online behavior of the patient; and
updating the machine learning algorithm based on the content viewership data, the online data, and behavior data.

4. The method of claim 3, wherein the additional resources comprise additional videos being available.

5. The method of claim 4, further comprising:
generating, via an updated machine learning algorithm, a modified healthcare questionnaire for use in future patient interactions.

6. The method of claim 4, wherein the behavior profile score of the patient is further based on how accurately the patient follows prescribed behavior.

7. The method of claim 1, further comprising:
recording audio of the patient as the answers are completed; and
identifying at least one audible expression of the patient made during completion of the behavioral questionnaire based on the audio of the patient made during the completion of the behavioral questionnaire,
wherein the numerical score is further based on the at least one audible expression.

8. The method of claim 1, wherein the physical medical condition is diabetes.

9. The method of claim 1, wherein the physical medical condition is associated with a cardiac condition.

10. A system, comprising:
a video capture device;
a processor; and
a computer-readable storage medium having instructions stored which, when executed by the processor, cause the processor to perform operations comprising:
receiving training data sets describing relationships between: (1) patients diagnosed with a physical illness, (2) patient health risk levels, and (3) patient trajectories without intervention;
training a neural network using the training data sets, resulting in a machine learning algorithm;
receiving, from a mobile device, answers to a behavioral questionnaire, wherein the answers are received in real-time as a patient self-reports answers to the behavioral questionnaire on the mobile device
recording, via the video capture device, a video of the patient as the answers are completed;
identifying, based on the video of the patient, at least one facial expression of the patient made during completion of the behavioral questionnaire;
identifying, based on the video of the patient, at least one repeated body posture of the patient made during completion of the behavioral questionnaire;
calculating a time period between instances of the at least one repeated body posture;
calculating a numerical score of the patient based upon the answers to the behavioral questionnaire, the time period, the at least one repeated body posture, and the at least one facial expression of the patient made during completion of the behavioral questionnaire;
receiving a physical medical condition of the patient; and
generating, by executing a playlist algorithm based on the physical medical condition of the patient using the physical medical condition of the patient and the numerical score, a playlist of videos associated with the physical medical condition
receiving a record of which videos within the playlist of videos were watched by the patient;
executing the machine learning algorithm, with inputs to the machine learning algorithm comprising the record and outputs of the machine learning algorithm comprising a modification to the playlist algorithm; and
modifying the playlist algorithm according to the modification.

11. The system of claim 10, wherein the playlist of videos associated with the physical medical condition are customized to the patient by:
identifying a plurality of portions corresponding to a plurality of videos, each portion in the plurality of portions being a video segment identified as relevant to the patient based upon the numerical score and the physical medical condition; and
caching the plurality of portions within a memory cache distinct from that of the plurality of videos, to yield the playlist of videos.

12. The system of claim 10,
wherein the training of the machine learning algorithm further comprises:
performing, via the processor, a regression on the training data sets, thereby identifying initial weights for the machine learning algorithm; and
the computer-readable storage medium having additional instructions stored which, when executed by the processor, cause the processor to perform operations comprising:
as the patient watches videos within the playlist of videos:
recording content viewership data regarding at least one of how patients view the playlist of videos, type of content viewed, and recently viewed videos in the playlist of videos;
calculating an online engagement pattern for the patient based on the content viewership data;
generating, by weighting at least one of: a clinically validated behavior score, the numerical score of the patient, demographic data associated with the patient, and the content viewership data, a behavior profile score of the patient;
identifying additional resources for the patient based on the behavior profile score, the physical medical condition, and the online engagement pattern;
receiving data indicating portions of the playlist of videos watched by the patient, to yield viewing data;
receiving online data identifying online behavior of the patient; and
updating the machine learning algorithm based on the content viewership data, the online data, and behavior data.

13. The system of claim 12, wherein the additional resources comprise additional videos being available.

14. The system of claim 13, the computer-readable storage medium having additional instructions stored which, when executed by the processor, cause the processor to perform operations comprising:
generating, via an updated machine learning algorithm, a modified healthcare questionnaire for use in future patient interactions.

15. The system of claim 13, wherein the behavior profile score of the patient is further based on how accurately the patient follows prescribed behavior.

16. The system of claim 10, the computer-readable storage medium having additional instructions stored which, when executed by the processor, cause the processor to perform operations comprising:
recording audio of the patient as the answers are completed; and
identifying at least one audible expression of the patient made during completion of the behavioral questionnaire based on the audio of the patient made during the completion of the behavioral questionnaire,
wherein the numerical score is further based on the at least one audible expression.

17. A non-transitory computer-readable storage medium having instructions stored which, when executed by a computing device, cause the computing device to perform operations comprising:
receiving training data sets describing relationships between: (1) patients diagnosed with a physical illness, (2) patient health risk levels, and (3) patient trajectories without intervention;
training a neural network using the training data sets, resulting in a machine learning algorithm;
receiving, from a mobile device, answers to a behavioral questionnaire, wherein the answers are received in real-time as a patient self-reports answers to the behavioral questionnaire on the mobile device
recording, via a video capture device, a video of the patient as the answers are completed;
identifying, based on the video of the patient, at least one facial expression of the patient made during completion of the behavioral questionnaire;
identifying, based on the video of the patient, at least one repeated body posture of the Patient made during completion of the behavioral questionnaire;
calculating a time period between instances of the at least one repeated body posture;
calculating a numerical score of the patient based upon the answers to the behavioral questionnaire, the time period, the at least one repeated body posture, and the at least one facial expression of the patient made during completion of the behavioral questionnaire;
receiving a physical medical condition of the patient; and
generating, by executing a playlist algorithm based on the physical medical condition of the patient using the physical medical condition of the patient and the numerical score, a playlist of videos associated with the physical medical condition;
receiving a record of which videos within the playlist of videos were watched by the patient;
executing the machine learning algorithm, with inputs to the machine learning algorithm comprising the record and outputs of the machine learning algorithm comprising a modification to the playlist algorithm; and
modifying the playlist algorithm according to the modification.

18. The non-transitory computer-readable storage medium of claim 17, wherein the playlist of videos associated with the physical medical condition are customized to the patient by:
identifying a plurality of portions corresponding to a plurality of videos, each portion in the plurality of portions being a video segment identified as relevant to the patient based upon the numerical score and the physical medical condition; and
caching the plurality of portions within a memory cache distinct from that of the plurality of videos, to yield the playlist of videos.

19. The non-transitory computer-readable storage medium of claim 17, wherein the training of the machine learning algorithm further comprises:
performing a regression on the training data sets, thereby identifying initial weights for the machine learning algorithm; and
the non-transitory computer-readable storage medium has additional instructions stored which, when executed by the computing device, cause the computing device to perform operations comprising:

as the patient watches videos within the playlist of videos:
    recording content viewership data regarding at least one of how patients view the playlist of videos, type of content viewed, and recently viewed videos in the playlist of videos;
    calculating an online engagement pattern for the patient based on the content viewership data;
    generating, by weighting at least one of: a clinically validated behavior score, the numerical score of the patient, demographic data associated with the patient, and the content viewership data, a behavior profile score of the patient;
    identifying additional resources for the patient based on the behavior profile score, the physical medical condition, and the online engagement pattern;
    receiving data indicating portions of the playlist of videos watched by the patient, to yield viewing data;
    receiving online data identifying online behavior of the patient; and
    updating the machine learning algorithm based on the content viewership data, the online data, and behavior data.

\* \* \* \* \*